United States Patent
Lennox

[19]
[11] Patent Number: 6,156,032
[45] Date of Patent: Dec. 5, 2000

[54] METHOD FOR CAUSING A STRICTURE OF A BODY PASSAGEWAY

[75] Inventor: Charles D. Lennox, Hudson, N.H.

[73] Assignee: Scimed Life Systems, Inc., Maple Grove, Minn.

[21] Appl. No.: 09/164,002

[22] Filed: Sep. 30, 1998

[51] Int. Cl.⁷ .................................................. A61B 18/14
[52] U.S. Cl. ............................... 606/41; 606/14; 606/21; 607/99; 607/105; 607/113
[58] Field of Search .................. 606/41, 45, 49, 606/14, 15, 21, 27; 607/99, 105, 113; 604/114

[56] References Cited

U.S. PATENT DOCUMENTS

| | | | |
|---|---|---|---|
| 5,520,684 | 5/1996 | Imran | 606/41 |
| 5,607,422 | 3/1997 | Smeets et al. | 606/41 |
| 5,626,576 | 5/1997 | Janssen . | |
| 5,681,282 | 10/1997 | Eggers et al. | 604/114 |
| 6,056,744 | 5/2000 | Edwards | 606/41 |

FOREIGN PATENT DOCUMENTS

| | | |
|---|---|---|
| WO 95/10978 | 4/1995 | WIPO . |
| WO 95/17131 | 6/1995 | WIPO . |

*Primary Examiner*—Lee Cohen
*Attorney, Agent, or Firm*—Testa Hurwitz & Thibeault L.L.P.

[57] ABSTRACT

This invention provides for an apparatus and method to cause a stricture in a body passageway. For example, urinary incontinence and vesicoureteral reflux can be treated by inserting an energy-delivering probe into the body passageway of the urinary tract and applying energy to an arcuate segment of the wall of the body passageway to cause injury to the wall, hyperplasia of the tissue surrounding the wall, and stricture of the body passageway. Other applications for the apparatus and method of the present invention includes treatment of gastro-esophageal reflux and fecal incontinence.

19 Claims, 6 Drawing Sheets

METHOD FOR CAUSING A STRICTURE OF A BODY PASSAGEWAY

TECHNICAL FIELD

This invention relates generally to the field of endoscopic medical procedures, and more specifically to the use of endoscopic probes for treating body passageway dysfunctions.

BACKGROUND INFORMATION

Urinary incontinence or, more specifically, urinary stress incontinence afflicts a large number of people. Although not life threatening, urinary incontinence has a dramatic negative impact on the quality of life. Vesicoureteral reflux is a congenital condition that afflicts one in one hundred children. In the more severe forms, reduced, or complete loss of kidney function can occur, and it can be life threatening.

Urinary incontinence results from dysfunctional urinary sphincter(s). The dysfunction of the sphincter(s) can be caused by disease, complications from urological procedures, or result from trauma to the pelvic region. The dysfunction of the sphincter(s) can also be caused by neurological or sphincter muscle dysfunction. In all cases, the sphincter is unable to retain urine in the bladder as normal.

Currently, there are several techniques and devices that are used to treat urinary incontinence. There are surgical solutions in which artificial sphincters are implanted into tissue surrounding the urethra. These artificial sphincters function as a valve and can be actuated by the patient. Other surgical implants are rubber-band like devices that are placed around the outside of the sphincter muscle and urethra and assist the sphincter in retaining urine. Some less invasive techniques involve the injection of bulking agents the submucosa of the urethra. The bulking agents can be biologically compatible materials such as Teflon, biomaterials such as bovine collagen, or autologous materials such as fat, collagen, muscle, or cartilage. Other therapies that are used include electrical stimulation of the sphincter muscle and biofeedback techniques.

Vesicoureteral reflux is similar to stress incontinence in that the vesicoureteric junction functions like a sphincter. The vesicoureteric junction is at the junction of the ureter and the bladder. In a normal vesicoureteric junction, the ureter joins the bladder through the muscularis mucosea of the bladder in an oblique fashion. During micturition, the muscularis mucosea contracts closing the ureter. Thus, the vesicoureteric junction acts as a check valve and prevents urine from flowing back into the kidney during bladder contraction during micturition. In an abnormal vesicoureteric junction, the ureter joins the bladder through the muscularis mucosea of the bladder in a perpendicular fashion. During micturition, the ureter remains open allowing the urine to flow back in the ureter. The backwards flow of urine and the associated pressurization of the ureter and kidney result in dilation of the ureter and scarring of the kidney. Interventional treatment of this condition consists of surgery and injection of bulking agents. Mild cases of reflux can be managed with medication.

SUMMARY OF THE INVENTION

It is an object of the invention to provide a treatment for both urinary incontinence and vesicoureteral reflux that is less intrusive than surgery or implantation of bulking agent, and that provides permanent relief It is another object of the present invention to provide a cure and/or relieve the symptoms of urinary incontinence and to preserve kidney function in people (e.g., children) afflicted with vesicoureteral reflux. The present invention is an improvement over other modalities such as surgical implants, or injectable tissue bulking agents for treating these conditions. This invention provides for a cost effective, minimally invasive, permanent treatment for urinary incontinence and vesicoureteral reflux without the need for implantation of foreign or autologous material.

More generally, this invention provides for bulking of a body passageway without introduction of bulking agents by causing disruption of epithelium lining the interior wall of the body passageway and injury to the submucosa to trigger a healing response that results in hyperplasia of the submucosa and stricture formation in the body passageway.

Methods and devices according to the present invention are used to form chronic stricture in a body passageway by the application of energy (e.g., RF energy) to create an injury to the wall of the body passageway and hyperplasia of the submucosa at the site of injury during the healing response. The hyperplasia of the submucosa at the site of the wound creates a stricture of the body passageway. More specifically, the invention involves inserting an energy-delivering probe into a body passageway and applying energy to a segment of the wall of the body passageway sufficient to create an injury to the wall, hyperplasia of the tissue adjacent the wall, and stricture of the body passageway.

Body passageways in which creation of a stricture may be desirable according to the present invention are the urethra, the ureters, the bile ducts, the esophagus, the rectum, veins and arteries, for example.

An endoscope can be used to insert energy-delivering probe according to the invention into the body passageway. The probe can have a focused energy emitter (pre-shaped to the desired shape of the injury) for applying the energy to the wall of the body passageway. The energy can be delivered to the wall in the form of, for example, heat, cryogen fluid, or mechanical abrasive action. Thus, the energy emitter can be a radio-frequency emitter (RF), an ultrasound emitter, a laser emitter, a cryogenic fluid emitter, or a mechanical abraser. The injury caused to the wall by the probe may be a burn or an abrasion. However the injury is caused, it results in a healing response that in turn results in hyperplasia at the site of the injury and stricture of the body passageway.

In some embodiments of the invention, incontinence is treated by causing a stricture of the urethra. The energy can be applied to a segment of the urethral wall proximal to the urethral sphincter. In other embodiments of the invention, vesicoureteral reflux is treated by causing a stricture of the ureter. The energy can be applied to a segment of the ureteral wall at the vesicoureteric junction. In yet other embodiments, gastro-esophageal reflux is treated by causing a stricture of the esophagus.

These and other objects, along with advantages and features of the invention disclosed herein, will be made more apparent from the description, drawings, and claims that follow.

BRIEF DESCRIPTION OF THE DRAWINGS

The foregoing and other objects, features and advantages of the present invention, as well as the invention itself, will be more fully understood from the following description of preferred embodiments, when read together with the accompanying drawings, in which.

DESCRIPTION

Figure 1B:
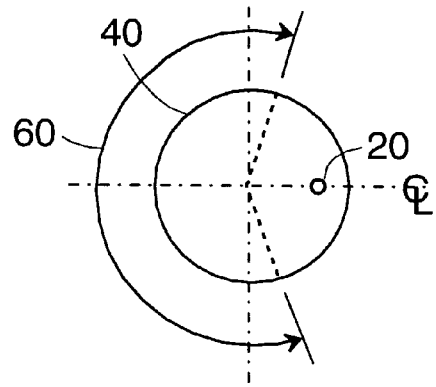
FIG. 1B is a top view of the probe of FIG. 1A.

This invention generally provides for a method and apparatus for forming a stricture in a body passageway. Stricture of a body passageway is desirable whenever there is a need to gain a better control over the passage of fluids within the body passageway. Varying degrees of stricture may be used with the methods and apparatus of the invention to obtain a gamut of treatment results. A stricture according to the present invention is a narrowing of a body passageway that decreases the flow or intermittently stops the passage of fluids within it upon contraction or relaxation of the surrounding tissue or the pressure of fluid within it, but does not result in a permanent occlusion of the body passageway.

In accordance with the invention, a stricture may be used, for example, in a body passageway of the urinary tract to cure or alleviate the symptoms of urinary incontinence and to preserve kidney function in persons (e.g., children) afflicted by vesicoureteral reflux. A stricture can also be formed in body passageways other than the urinary tract such as, the bile duct, the vascular system, and the digestive system, for example. Thus, a stricture may be used in veins, for example, to treat tumors by decreasing or stopping blood flow to benign or cancerous neoplasms. Strictures in arteries may be used, for example, in by-pass heart surgery, liver transplant or kidney transplant. Strictures in the rectum may be used to treat fecal incontinence. Strictures in the esophagus at the gastro-esophageal junction may be used to treat gastro-esophageal reflux.

A stricture according to the invention may create a valve action, open and shut, within the body passageway upon contraction or relaxation of the smooth muscle cells surrounding the body passageway or by the variation of pressure within the body passageway. In a shut position, the supple and compliant wall of the body passageway is collapsed and pressed against the non-compliant, fibrous hyperplasic mass forming the stricture. In an open position, the wall of the body passageway opposite the stricture is extended and is not in contact with the hyperplasic mass.

Preferred body passageways for treatment according to the apparatus and method of the present invention are lined with epithelium cells. The epithelium, such as the urothelium in the urinary tract or the endothelium in the vascular system, belongs to a category of cells that are continuously replicating to replace destroyed cells. Smooth muscle cells that populate the submucosa are in normal condition quiescent, stable cells that show a low level of replication. However, in response to stimuli, such as following injury, these cells can undergo rapid division. This rapid cell division can lead to hyperplasia at the site of the injury. De-epithelization can be such an injury stimulating hyperplasia.

Hyperplasia is an increase in the number of cells in a tissue, such as the submucosa, which results in an increase in volume of body tissue. It is a response of connective tissue cells that occurs during wound healing. Hyperplasia is stimulated by growth factors released from the injured cells. Hyperplasia is best induced when the extracellular matrix of the epithelium and the basal membrane have been destroyed sufficiently to expose the cells of the submucosa to growth factors released from injured cells. Therefore, it is believed that the epithelium has a modulating effect on the mitotic cycle of the muscle cells in the submucosa such that the preservation of the epithelium will prevent hyperplasia of the muscle cells underlying the intact epithelium even if adjacent tissue is de-epithelized and injured. Thus, it is believed that the degree of stricture formation is proportional to the degree of injury, and that the stricture morphology is hyperplasia of muscle cells in the submucosa.

Hyperplasia is generally an undesirable result of wound healing. For example, if it occurs in the skin, it would leave scars. However, it can be advantageously induced in the body passageways of the urinary tract, for example, to assist in preventing the unwanted urine flow such as in the treatment of urinary incontinence or vesicoureteral reflux.

In accordance with this invention, an injury-causing probe, such as an energy-emitting probe, is introduced into the body passageway via an endoscope. Access to the urethra is direct, as it directly communicates with the exterior of the body. Access to the ureter is achieved via the urethra and bladder. Access to veins and arteries is percutaneous. Access to the bile duct may be percutaneous or through the upper gastro intestinal tract, i.e. through the mouth, the esophagus, the stomach and the duodenum. Access to the rectum is direct. Access to the esophagus is achieved through the mouth. Methods to monitor the positioning of the probe within the body passageway are well known in the art. In preferred embodiments, positioning of the probe in the body passageway may be monitored by the use of an endoscope, fluoroscopy or other locating and positioning devices.

Once the probe is positioned at the location of the desired bulking, energy is applied to create an injury in the wall of the body passageway, such that a radial segment of the epithelium covering the wall along a circumferential portion of the body passageway, i.e., radial or arcuate segment, is destroyed and removed, exposing the submucosa. The remaining radial segment, within the same circumferential portion of the body passageway, is preferably left un-injured by the probe. The preservation of the epithelium in the complementary radial segment within the same circumferential portion of the body passageway will insure that the hyperplasia occurring during the wound healing process does not result in an occlusion of the body passageway by adhesion of the opposite surfaces of the wall.

The nature of the injury created at the site of the desired bulking is of a type where the extracellular matrix is denatured and where stimulating growth factors are released from the injured cells. Alternatively, stimulating growth factors may be provided to the site of the injury by direct application using the cooling channel of the probe or by parenteral oral mode of administration. Injuries such as burns created by heating or freezing would be suitable. Also, injuries created by an abrasion, are suitable for the methods of the present invention. In preferred embodiments, the injury is created as a burn by the application of heat from an RF probe.

Figure 8A:
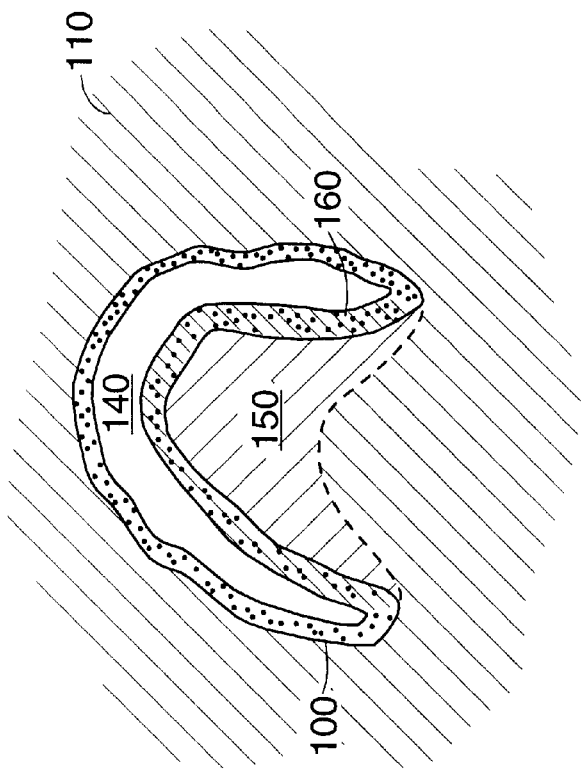
FIGS. 8A and 8B are schematic cross-sectional representations illustrating the valve action of opening and closing, respectively, of a stricture of a body passageway following treatment according to the invention.
Figure 8B:
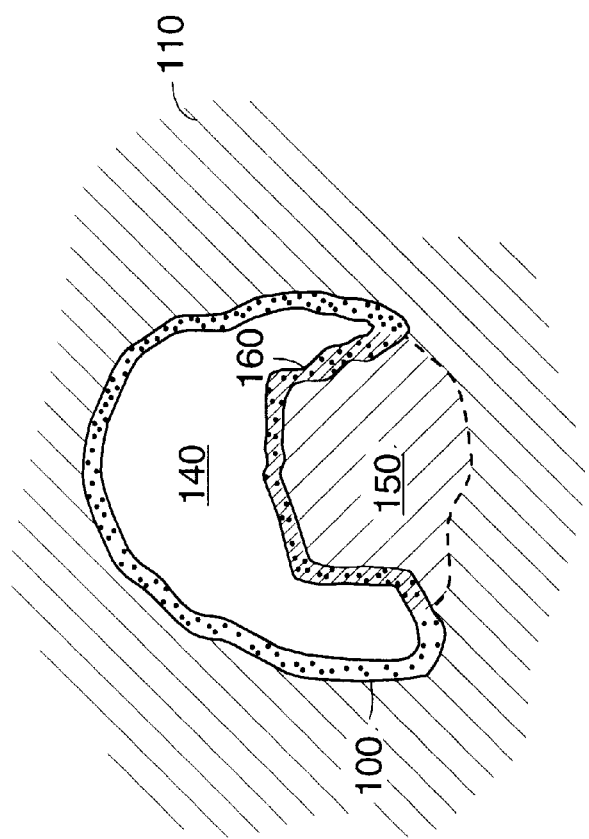

The injury can take a variety of sizes and shapes as long as the shape of the resulting hyperplasia be conducive of a valve action within the body passageway, i.e., constricting the body passageway in a relaxed or contracted state of the body passageway (as shown in FIG. 8A) and unobstructing the body passageway in a expanded state of the body passageway (as shown in FIG. 8B). Both the size and shape of the injury are controlled by the size and shape of the energy emitting zone of the energy emitter on the outer surface of the probe. The depth of the injury can be controlled by the amount of energy delivered to the surface of the wall of the body passageway. In some embodiments, the shape of the injury is an arcuate quadrangular segment. A quadrangular shape is any polygonal shape having four sides and four corners including, but not limited to, squares, rectangles, losanges, and trapezia. In preferred embodiments, the shape of the injury is an arcuate rectangular segment. In certain embodiments, the shape of the injury is a continuous segment. In yet other embodiments, the shape of the injury is a series of proximate, non-contiguous segments. In yet other embodiments, the shape of the injury is a series of proximate, non-contiguous segments on alternate, opposite sides of the wall of the body passageway.

In cases where hyperplasia of the total circumference of the body passageway is desired to achieve a greater control of the passage of fluid, the procedure may be repeated after the first injury has completely healed, i.e., after total epithelization of the hyperplasic mass at the site of the injury. A subsequent injury can then be caused to a new portion of the body passageway adjacent to the prior site of injury, either within the same circumferential portion, or along the longitudinal axis of the body passageway. The subsequent injury can also be repeated at the same location as the prior injury, or at a location overlapping the prior injury until the desired bulking is reached. Thus, by repeating this procedure a number of times, hyperplasia to the complete circumference of the body passageway may be attained, this, however, without inducing total occlusion of the body passageway.

The size of the injury in the case of the urethra or the ureters for example, can be about 0.2–1 mm in depth, about 4–20 mm in length over about a 30 to 180 degree angle. In preferred embodiments, the size of the wound is 0.4 to 0.8 mm in depth, 8 to 12 mm in length, and 60 to 120 degree angle. In a most preferred embodiment, the size of the wound is 1 mm in depth, 10 mm in length over a 60 degree angle. In the case of the esophagus or rectum, the length of the injury can be 3–5 cm., the depth and the width being as described above.

It is understood that the shape of the desired stricture within the body passageway may easily be designed and controlled by the manner in which and the location at which the wall is injured. Design of injury to attain a specific stricture pattern is well within the reach of a skilled artisan. The present invention is not to be limited by the above-described specific stricture patterns.

A probe designed to carry out the above described treatment can be used through the working channel of an endoscope. The probe can be flexible to facilitate the positioning within the body passageway, such as in the ureter, or the esophagus for example. In a preferred embodiment, the diameter of the probe is 6 to 10 French or about that size for body passageways of the urinary tract. In another preferred embodiment, the diameter of the probe is 30–40 French or about that size for body passageways of the gastrointestinal tract. The distal end of the probe is fitted with an energy emitter. Alternatively, the distal end of the probe may be an expandable balloon with an energy emitter fitted onto a portion of its outer surface. Optionally, the distal end also includes a thermistor or thermal sensor to ensure the controlled delivery of sufficient energy to create an injury to the epithelium as described above. To this end, the probe may also include a cooling channel for the delivery of cooling fluid to the site of injury. The cooling channel may also be used for delivery of drugs, such as, but not limited to, anesthetics, antibiotics, antiseptics, growth factors and pharmaceutical compositions thereof, to the site of the injury.

The size and shape of the energy emitter at the periphery of the probe can be preformed to correspond to the desired size and shape of the injury. The size of the energy emitter at the periphery of the probe may be defined and measured by two parameters: a height (h) and an arc ($\theta$). The height (h) is measured by the distance separating the two most extreme points following a line parallel to the longitudinal axis of the probe. The arc is measured by the angle formed by two planes intersecting along the central axis of the probe and each passing by the most extreme lateral points of the energy emitter at the peripheral surface of the probe. In some embodiments, the energy emitter at the periphery of the probe has an arcuate quadrangular shape. In preferred embodiments, energy emitter at the periphery of the probe has an arcuate rectangular shape. In certain embodiments, the energy emitter has a shape of a continuous segment. In yet other embodiments, the energy emitter has a shape of a series of proximate, non-contiguous segments. In yet other embodiments, the energy emitter has a shape of a series of proximate, non-contiguous segments on alternate, opposite sides of the distal end of the probe. The remaining circumferential portion of the probe is made of insulating material to prevent injury to the epithelium neighboring the site of the desired injury. Synthetic or natural polymers can be suitable as insulating material for use in the manufacture of the probe.

Figure 1A:
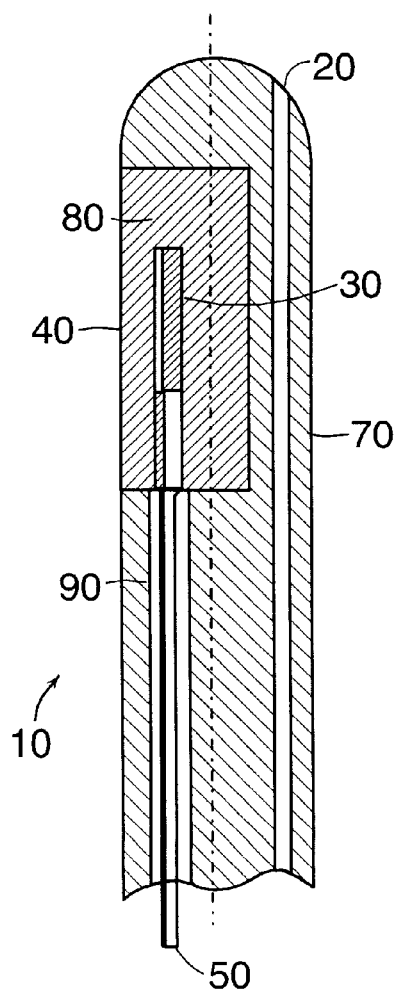
FIG. 1A is a cross-sectional side view of an embodiment of a probe according to the invention.
Figure 2:
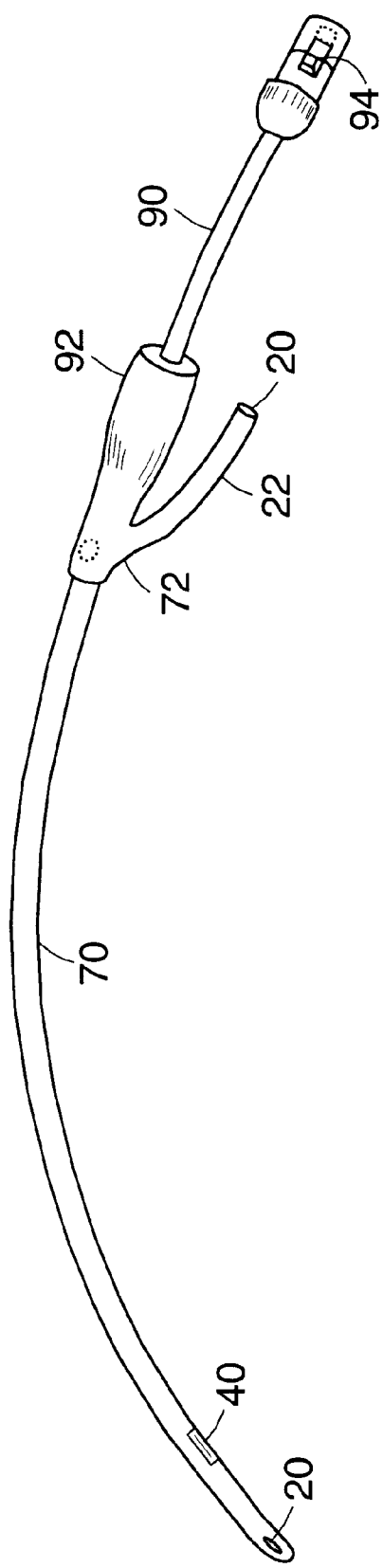
FIG. 2 is a perspective view of the energy-delivering device of FIGS. 1A and 1B.

Suitable energy emitters include radio-frequency (RF) emitters, ultrasound emitters, laser emitters, electrical heat emitters, cryogenic fluid emitters, or mechanical abraser. FIGS. 1A and 1B show two views of an RF emitter suitable to carry out the methods of the present invention. FIG. 2 shows a side view of a device featuring a RF emitter at its distal end suitable to carry out the methods of the present invention. Examples of emitters that may be suitable or use in the treatments described herein include those described in: U.S. Pat. No. 5,122,137 for temperature controlled RF delivering probe; U.S. Pat. No. 5,383,876 for a fluid cooled electrosurgical heat delivering probe; U.S. Pat. No. 5,380,317 for a localized high intensity light and heat delivering probe; U.S. Pat. No. 4,662,368 for a localized heat delivering probe; and U.S. Pat. No. 4,765,331 for a focused heat delivering probe with an treatment arc of less than 360 degrees. All of these patents are hereby incorporated herein by reference. In general, the emitters described in these patents are suitable to the extent that they can be made to fit within the urinary passageways and deliver energy sufficient to create an injury as described herein.

In embodiments where the energy is delivered in the form of thermal energy, an RF electrode as shown in FIGS. 1A and 1B can be disposed on the distal end of the device shown in FIG. 2. The RF electrode can deliver a suitable level of energy at the site of the desired injury when a temperature of about 45° C. to about 100° C. is maintained for a period of about 1 to about 60 seconds. The length of time for application of energy varies inversely with the temperature applied at the site of the injury. For example, suitable injuries for this invention can be created with the application of 100° C. for about one second. Suitable injuries can also be created with the application of 60° C. for about 10 seconds, or even 48° C. for about sixty seconds. In a preferred embodiment, the injury is created with the application of RF energy that provides 60° C. at the desired site of injury for 10 seconds. It will be apparent to a skilled artisan that many variations as to the temperature and length of time of heat application can result in an injury of the type according to the invention.

In one embodiment, the apparatus for accomplishing the methods of the present invention can apply heat using an RF probe 10 as shown in FIG. 1A with a grounding plate (not shown). The probe 10 is made of a shaft 70 having a cooling channel 20 located within the shaft 70, running along the longitudinal axis of the shaft 70. An electrode 40 is located at the distal end of shaft 70. The electrode 40 comprises a conductive material 80 having an arcuate quadrangular shape at the periphery of the shaft 70. The conductive material 80 is in contact with a thermistor 30. The thermistor is connected to a RF power supply (not shown) via wires 50 running through a wire channel 90.

Alternatively, the probe 10 can comprise a temperature sensor (not shown) to permit indirect monitoring of the application of heat to the tissue and thus control the degree of injury to the tissue. The sensor would be connected to a control circuit that modulates RF power applied to the electrode according to the signal received from the temperature sensor. The control circuit and an RF power supply would alternate between two operating modes. In a first mode, the RF power supply would apply RF power to the electrode. In a second mode, the control circuit would sense a signal from the temperature sensor in the absence of RF signal. The control circuit then would compare the signal from the temperature sensor to a set value (determined by the operator) and modulate the RF power applied to the electrode in accordance with the set value.

FIG. 1B shows a top view of probe 10 showing the arcuate shape 60 having an arc θ of the electrode 40 at the periphery of the shaft 70. FIG. 2 shows the device with a flexible shaft 70 having a radial quadrangular electrode 40 at its distal end and a connector 72 having a port 22 for the cooling channel 20 and a port 92 for the wire channel 90. The wire channel 90 is connected to an adapter 94 for connecting wires 50 with an RF power supply (not shown).

Suitable conductive materials 80 for the electrode 40 are materials that present little ohmic resistance. For example, metals such as metal from group VIII and IB or alloy thereof are suitable materials. Preferably, the conductive materials is copper or platinum.

Suitable materials for the shaft 70 and distal portion of the probe surrounding the electrode are synthetic materials and insulants. For example, silicone, rubber, latex, polyurethane, nylon, polyethylene are suitable materials, as well as any other suitable catheter material.

The following description explains in more details one embodiment of the methods and apparatus of the present invention for treatment of the urinary tract dysfunctions.

Figure 3:
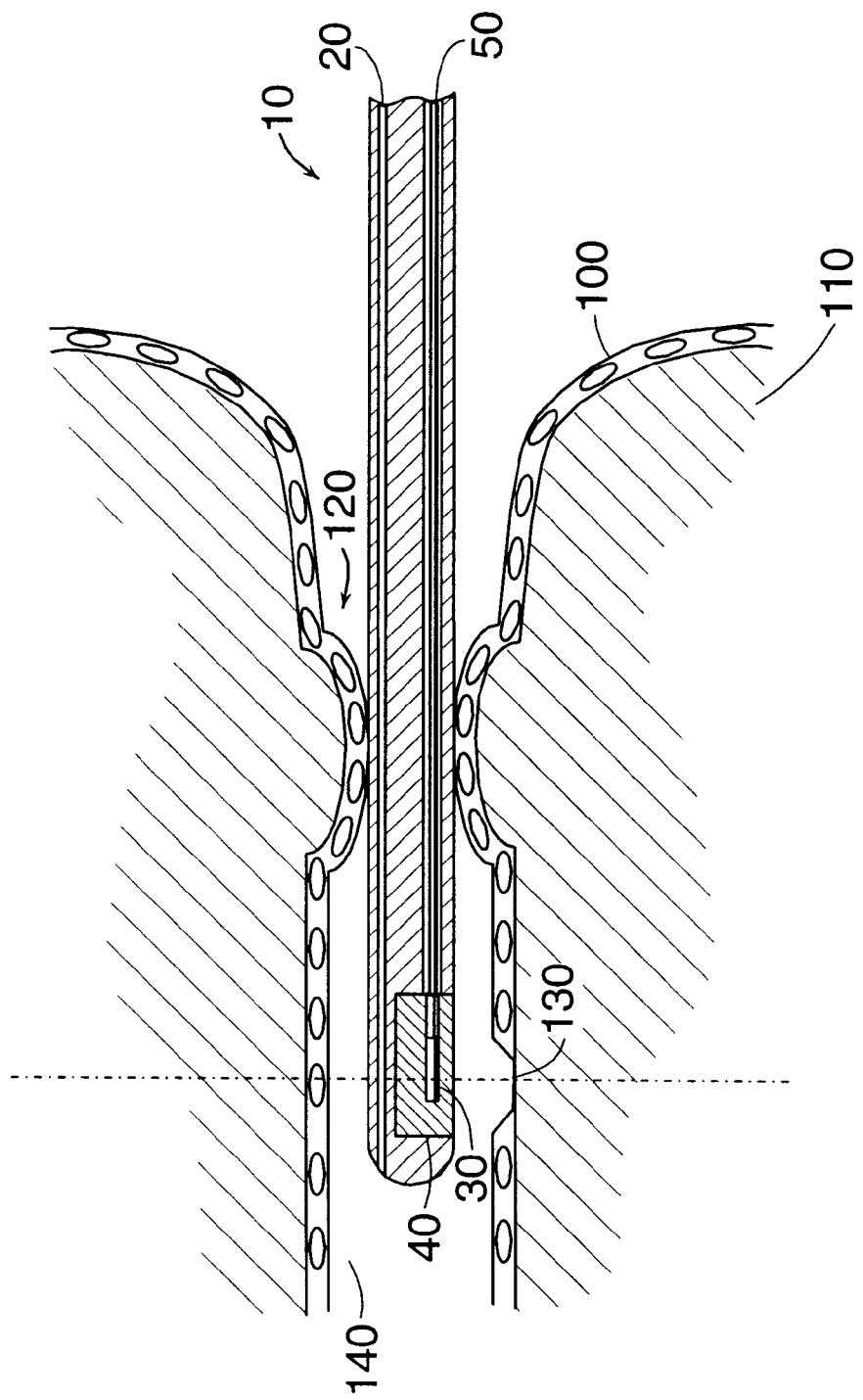
FIG. 3 is a longitudinal cross-sectional view showing the use of the probe (FIGS. 1A, 1B and 2) during treatment.
Figure 5:
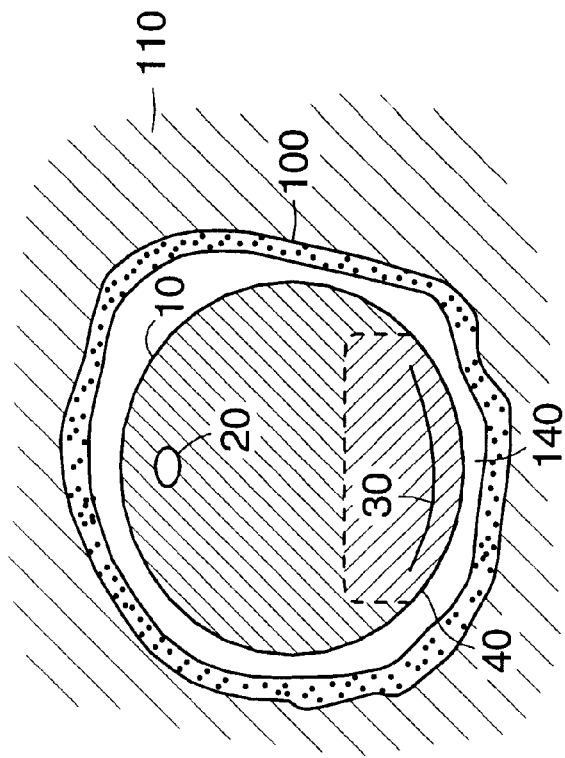
FIG. 5 is a schematic cross-sectional representation illustrating the use of a probe during treatment according to the invention prior to causing injury to the wall of the urethra.
Figure 4:
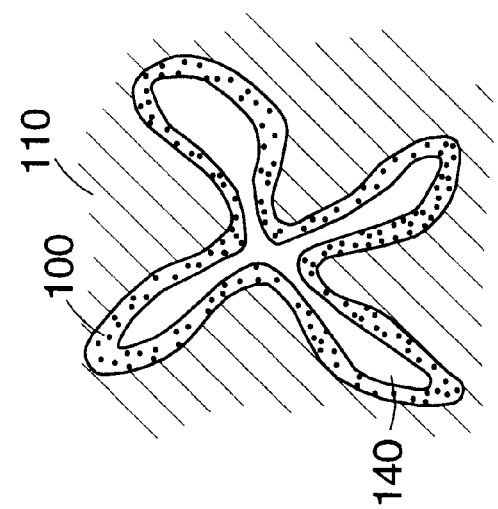
FIG. 4 is a schematic cross-sectional representation of a body passageway prior to treatment according to the invention.
Figure 7:
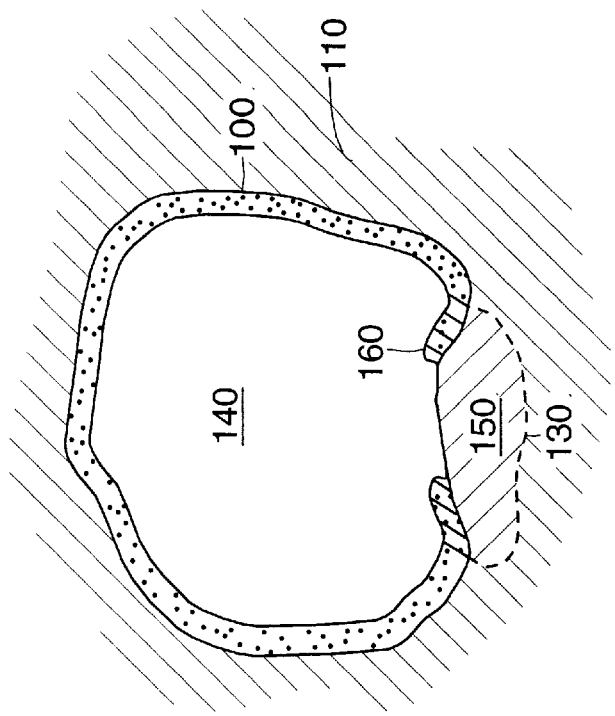
FIG. 7 is a schematic cross-sectional representation illustrating the healing response following treatment according to the invention.
Figure 6:
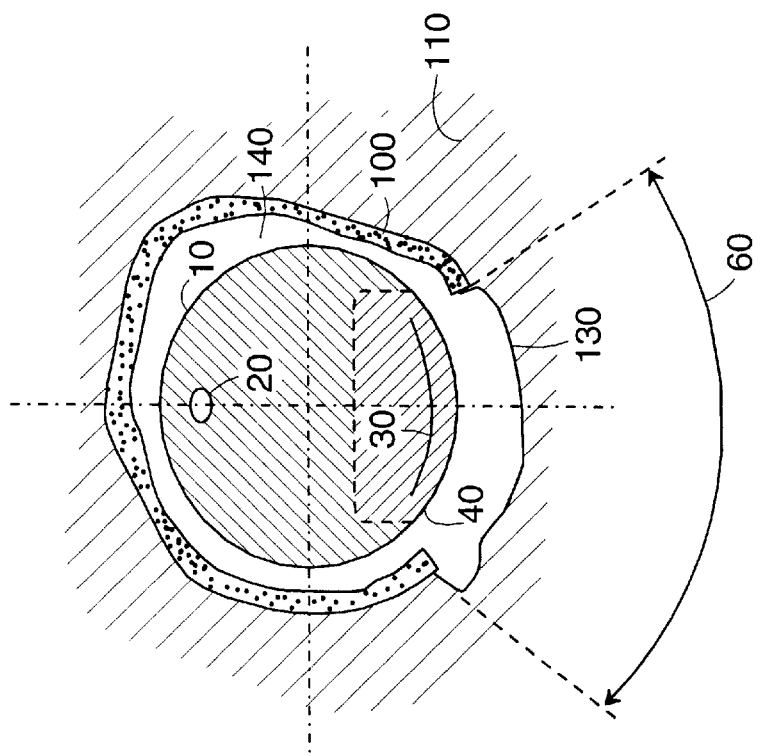
FIG. 6 is a schematic cross-sectional representation illustrating the use of a probe during treatment according to the invention after causing injury to the wall of the urethra.

As an example, FIG. 3 shows the probe 10 positioned within the lumen 140 of the urethra of a human female. The electrode 40 is located in the proximity of the urethral sphincters 120. In a human male, the probe would be inserted through the penile urethra, the bulbous urethra, and positioned in the prostatic urethra beyond the urethral junction with the prostate duct (not shown). Opposite the electrode, an injury 130 to the epithelium 100 of the urethra exposes the submucosa 110. Prior to insertion of the probe 10 and referring to FIG. 4, the lumen 140 of the urethra is collapsed and folded more or less loosely by the pressure of the surrounding tissues, the submucosa 110 and epithelium 100. Referring to FIG. 5 which shows a cross-sectional view along the axis shown in FIG. 3, the probe 10 is located within the lumen 140 of the urethra prior to the application of heat. The lumen 140 is shown expanded by the circular shape of the probe 10. The electrode 40 is in close proximity of the epithelium 100 of the urethra. Referring to FIG. 6 which shows a cross-sectional view along the axis shown in FIG. 3, the probe 10 is located within the lumen 140 of the urethra after the application of heat. The application of heat has removed a radial segment 60 of epithelium 100 and submucosa 110 at the site of the injury 130. The size and shape of the injury 130 correspond to the size and shape of the electrode 40. Following application of heat and destruction of the epithelium 100, and referring to FIG. 7, a healing response is triggered that stimulates the cells of the submucosa 110 to divide leading to hyperplasia of the submucosa 150. Cells division continues until the newly grown epithelium 160 has covered the site of injury 130. Referring to FIGS. 8A and 8B, the hyperplasia 150 at the site of injury 130 once the new epithelium 160 has fully regrown protrudes into the lumen 140 of the urethra. FIGS. 8A and 8B illustrate the valve action when the urethra is expanded by the pressure of the passage of urine in the lumen 140, as in FIG. 8A, and when the urethra is collapsed by the pressure of the surrounding tissues of the submucosa 110, as in FIG. 8B closing the flow of urine in the lumen. The valve action is due to the difference in texture between the hyperplasic mass and the opposite wall of the body passageway. Hyperplasic growth is fibrous in nature and thus non compliant while the remaining of body passageway is compliant. Thus, the hperplasic fibrous mass presses against the compliant opposite wall when the body passageway is collapsed as in FIG. 8B and operate as a valve.

Having described certain embodiments of the invention, it will now become apparent to one skilled in the art that other embodiments incorporating the concepts disclosed herein may be used without departing from the spirit of the invention. Therefore, it is intended that the scope of the present invention be only limited by the following claims.

What is claimed is:

1. A method for causing a stricture of a body passageway, comprising the steps of inserting an energy-delivering probe into a body passageway, the body passageway defined by an internal tubular wall and adjacent tissue surrounding the wall; and applying energy along a radial segment of the wall using said probe, thereby causing injury to the wall, hyperplasia of tissue adjacent the wall, and stricture of the body passageway.

2. The method of claim 1, wherein the body passageway is the urethra.

3. The method of claim 2, wherein the energy is applied proximal to the urethral sphincter.

4. The method of claim 1, wherein the body passageway is the ureter.

5. The method of claim 4, wherein the energy is applied at the vesicoureteric junction.

6. The method of claim 1, wherein the body passageway is the bile duct.

7. The method of claim 1, wherein the body passageway is a vein or an artery.

8. The method of claim 1, wherein the application of energy causes a burn.

9. The method of claim 8, wherein the energy is RF radiation.

10. The method of claim 1, wherein the energy is applied through an energy emitter near a distal end of the probe.

11. The method of claim 10, further comprising the step of regulating the temperature of the energy emitter.

12. The method of claim 1 further comprising the step of
applying energy along a segment of the wall causing a subsequent injury to the wall, hyperplasia of tissue surrounding the wall and tighter stricture of the body passageway.

13. The method of claim 12 wherein a subsequent injury is caused at a location overlapping the prior injury.

14. The method of claim 1, wherein the body passageway is the rectum.

15. The method of claim 1, wherein the body passageway is the esophagus.

16. A method for treating urinary incontinence by causing a stricture in a urethra, said method comprising the steps of
inserting an energy-delivering probe into the urethra, the urethra having a tubular internal wall and adjacent tissue surrounding the wall, said energy-delivering probe having a temperature regulated RF electrode near a distal end of said probe; and applying energy along a radial segment of the wall through said electrode, thereby causing injury to the wall, hyperplasia of tissue adjacent the wall, and stricture of the urethra.

17. The method of claim 16, wherein the energy is applied proximal to the urethral sphincter.

18. A method for treating vesicoureteral reflux by causing a stricture in a ureter, said method comprising the steps of
inserting an energy-delivering probe into the ureter, the ureter having a tubular internal wall and adjacent tissue surrounding the wall, said energy-delivering probe having a temperature regulated RF electrode near a distal end of said probe; and applying energy along a radial segment of the wall through said electrode, thereby causing injury to the wall, hyperplasia of tissue adjacent the wall, and stricture of the urethra.

19. The method of claim 18, wherein the energy is applied at the vesicoureteric junction.

* * * * *